(12) United States Patent
Thomas et al.

(10) Patent No.: US 10,968,161 B2
(45) Date of Patent: Apr. 6, 2021

(54) SYNTHESIS AND PURIFICATION OF MUCONIC ACID ESTER FROM ALDARIC ACID ESTERS

(71) Applicant: Teknologian tutkimuskeskus VTT Oy, Espoo (FI)

(72) Inventors: David Thomas, Espoo (FI); Juha Linnekoski, Espoo (FI); Martta Asikainen, Espoo (FI); Nicolaas Van Strien, Espoo (FI); Anneloes Berghuis, Espoo (FI)

(73) Assignee: Teknologian tutkimuskeskus VTT Oy, Espoo, FL (US)

( * ) Notice: Subject to any disclaimer, the term of this patent is extended or adjusted under 35 U.S.C. 154(b) by 0 days.

(21) Appl. No.: 16/968,615

(22) PCT Filed: Feb. 11, 2019

(86) PCT No.: PCT/FI2019/050099
§ 371 (c)(1),
(2) Date: Aug. 10, 2020

(87) PCT Pub. No.: WO2019/155128
PCT Pub. Date: Aug. 15, 2019

(65) Prior Publication Data
US 2021/0047260 A1    Feb. 18, 2021

(30) Foreign Application Priority Data
Feb. 9, 2018  (FI) ..................... 20185119

(51) Int. Cl.
*C07C 67/54*    (2006.01)
*C07C 67/327*   (2006.01)
*C07C 67/03*    (2006.01)

(52) U.S. Cl.
CPC .............. *C07C 67/54* (2013.01); *C07C 67/03* (2013.01); *C07C 67/327* (2013.01)

(58) Field of Classification Search
CPC ........ C07C 67/54; C07C 67/03; C07C 67/327
See application file for complete search history.

(56) References Cited

U.S. PATENT DOCUMENTS

| | | |
|---|---|---|
| 2,324,088 A | 7/1943 | Jewett |
| 2017/0001944 A1 | 1/2017 | Zhang et al. |

FOREIGN PATENT DOCUMENTS

| | | |
|---|---|---|
| GB | 943721 A | 12/1963 |
| JP | 2008127282 A | 6/2008 |
| WO | WO9629347 A1 | 9/1996 |
| WO | WO2015189481 A1 | 12/2015 |
| WO | WO2016032403 | * 3/2016 |
| WO | WO2016032403 A1 | 3/2016 |
| WO | WO2017/207875 | * 12/2017 |
| WO | WO2017207875 A1 | 12/2017 |

OTHER PUBLICATIONS

Li et al: Highly efficient chemical process to convert mucic acid into adipic acid and DFT studies of the mechanism of the rhenium-catalyzed deoxydehydration. Angew. Chem. Int. Ed., Mar. 12, 2014, vol. 53, p. 4201.

* cited by examiner

*Primary Examiner* — Yevgeny Valenrod
*Assistant Examiner* — Blaine G Doletski
(74) *Attorney, Agent, or Firm* — Laine IP Oy

(57) ABSTRACT

According to an example aspect of the present invention, there is provided a method for producing muconic acid ester from aldaric acid ester, and for separating and purifying the produced muconic acid ester by high vacuum distillation in a total heating environment.

19 Claims, 1 Drawing Sheet

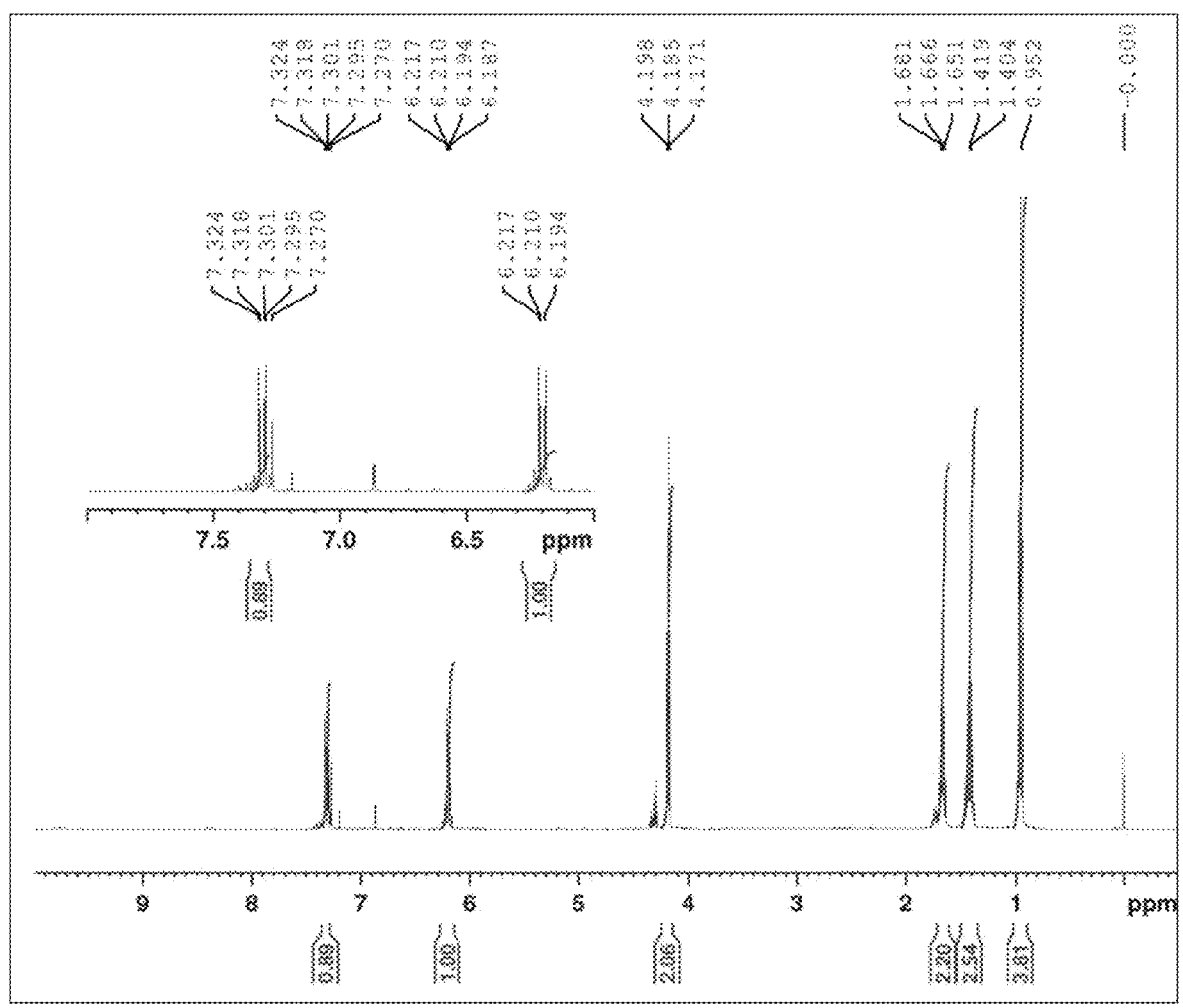

SYNTHESIS AND PURIFICATION OF MUCONIC ACID ESTER FROM ALDARIC ACID ESTERS

FIELD

The present invention relates to an improved method for converting aldaric acid to muconic acid. In addition, the present invention relates to purification of the produced muconic acid by utilizing high vacuum distillation in a total heating environment.

BACKGROUND

Muconic acid (IV) and muconic acid esters (V, VI) may be produced via the hydrodeoxygenation of aldaric acids (I). Aldaric acids, such as galactric acid or glucaric acid, can be produced from pectin, starch and other carbohydrates both edible and non-edible. By converting aldaric acids to muconic acid, a doorway is opened which allows for a wide variety of compounds to be prepared from bio-based resources, which would otherwise be prepared from crude oil stock. WO 2015/189481 describes the production of sugar acid platform chemicals, more precisely muconic acid, from aldaric acid(s) via selective catalytic hydrodeoxygenation. This method can be efficient but it requires a high dilution and catalyst concentration. The resultant product is typically afforded in low to good yield (17-70%), but the methyltrioxorhenium catalyst (MTO) is highly expensive and catalyst reuse is a challenge.

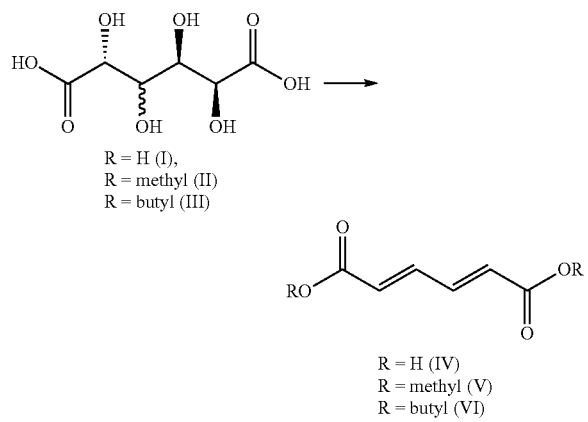

R = H (I),
R = methyl (II)
R = butyl (III)

R = H (IV)
R = methyl (V)
R = butyl (VI)

Biotechnically muconic acid can be produced via microorganisms, but the yield is limited to approximately 35% due to the efficiencies inherit in using microorganisms that also require carbohydrate feedstock.

Continuous production of muconic acid from saccharic acid using ammonium perrhenate is also possible (WO 2017/207875), however, this is carried out by using an alternative aldaric acid (glucaric acid) and a continuous flow reactor (CFR) rather than a batch reactor. The CFR has, unlike the batch reactor, a low dilution, low contact time between reagents and catalysts and is also run at a lower temperature. The batch reactor process uses a higher concentration for a predetermined amount of time and at a set temperature where there is greater contact time between reagents and catalyst.

The synthesis of bio-based monomers from sugars and sugar acids is well documented in the scientific and patent literature. However, typically the finer details of down-stream processing are absent, chiefly the purification step. Crystallization techniques to afford pure material are often expensive and require a lot of solvent, for example, column chromatography or recrystallization making them unsuitable for large scale-up. Large molecules, especially highly polar compounds such as carboxylic acids, which melt above 100° C. are often prone to destruction upon distillation due to the high temperature needed to vaporize the components, in additions to mechanic problems encountered when distillation products crystallize on cold surfaces normally intended for liquefaction to occur. Muconic acid esters are typically purified by either re-crystallization, which uses a lot of solvent and possess a fire hazard, or by column chromatography, which in turn is slow, uses a lot of solvent and is limited in terms of volume; neither of these methods are suited to industrial scale-up due to safety concerns and environmental concerns.

To suite for polymerization in high-end applications, the monomer itself needs to be of high purity, often greater than 99.5%. Impurities can cause, for example, failure of the polymerization and problems with the final product application. Thus, there is a need for a cost efficient and scalable method for both producing muconic acid from aldaric acids, and for separating and purifying the produced muconic acid (ester) from the crude reaction mixture.

SUMMARY OF THE INVENTION

The invention is defined by the features of the independent claims. Some specific embodiments are defined in the dependent claims.

According to an aspect of the present invention, there is provided a method for producing muconic acid ester from aldaric acid, especially from aldaric acid ester, such as mucic acid ester.

According to another aspect of the present invention, there is provided a method for separating and purifying the produced muconic acid ester from a crude reaction mixture by utilizing high vacuum distillation in a total heating environment.

These and other aspects, together with the advantages thereof over known solutions that are achieved by the present invention, as hereinafter described and claimed.

The method for producing muconic acid and its esters is characterized by what is stated in the characterizing part of claim 1.

The method for separating and purifying muconic acid is mainly characterized by what is stated in the characterizing part of claim 11.

Considerable advantages are obtained by means of the present invention. These include, for example, reduced use of solvent due to higher raw material solubility, reduced use of catalyst because of increased efficiency, the potentially for reuse, increased yield of reaction making side-product problems less significant, cleaner reactors since the reaction is more efficient and higher yielding, which reduces the clean-down time between reactions. Also, when using ammonium perrhenate the use of hydrogen can be avoided, thus making the process more environmentally friendly and safer (less explosion risk). Using ammonium perrhenate catalyst especially improves the reaction costs since it is considerably cheaper than methyltrioxorhenium (MTO). High vacuum distillation in a total heating environment is enough to allow the efficient recovery of muconic acid ester in high recovery and purity from the reaction mixture. Furthermore, the methods of the present inventions are scalable up to large volumes.

Next, the present technology will be described more closely with reference to certain embodiments.

EMBODIMENTS

The present technology provides efficient methods for producing muconic acid ester from aldaric acid or its ester, such as mucic acid ester, and for purifying the produced muconic acid ester by utilizing high vacuum distillation in a total heating environment.

FIG. 1 is a 1H NMR diagram showing the muconic acid butyl ester peaks after Kugelrohr distillation.

One embodiment of the present invention is a method for producing muconic acid from aldaric acid, wherein the method includes at least the steps of:
- esterification of the aldaric acid into aldaric acid ester,
- catalytic hydrodeoxygenation of the aldaric acid ester by heating the aldaric acid ester with a solvent and optionally a reductant and/or an acid catalyst in a pressurized container to temperatures between 120 to 220° C. in the presence of a transition metal catalyst for a pre-determined reaction time, and
- purifying the produced muconic acid ester in a total heating environment.

By making the raw material aldaric acid, such as mucic acid into the ester form, the solubility is increased, which allows the reaction to be more concentrated, reducing the working solvent equivalents from 30 to 10 or less. Once esterified, the yield can be significantly increased due to improved solubility.

In one embodiment of the present invention, catalytic temperatures between 150 and 200° C., preferably of about 175° C. are used to produce muconic acid and its esters when using ammonium perrhenate. When MTO is employed, the catalytic temperature is between 100-150° C., preferably 120° C.

One important aspect of the invention is to select an efficient and functional combination of catalyst, solvent and reductant. The inventors of the present invention have managed to develop a combination, which facilitates the use of light (i.e. short) alcohols, such as methanol, ethanol and n-butanol, for the reduction step, thus providing excellent results towards the desired end-products.

Thus, according to one embodiment of the present invention, the catalyst is selected from ammonium perrhenate or methyl trioxo rhenium, preferably ammonium perrhenate.

Methyltrioxorhenium is an efficient catalyst but it is expensive and difficult to recycle. By using the mucic acid ester there is more contact between the mucic acid ester and catalyst and hydrogen since it is dissolved into the reaction mass. This makes it more feasible to use MTO since the yield obtained can be consistently high. The reaction time is also significantly lowered from the original 48 hours to 2-6 hours.

Ammonium perrhenate by comparison is cheap and is the most commonly traded form of rhenium. This allows the reaction to be run at a higher concentration, using less catalyst and with an improved reaction yield. Also, ammonium perrhenate is a heterogeneous catalyst allowing it to be readily filtered from the reaction mixture. This gives the potential for the reuse of catalyst. The reaction is efficient at 175° C. compared to 120° C. when using MTO. Additionally, ammonium perrhenate catalyst allows the reaction time to be reduced considerably when compared to the original process, 2-12 hours verses 48 hours. By preferentially using ammonium perrhenate the reactor is notably cleaner after the reaction and can be quickly cleaned-out without any significant or problematic heavy mechanical cleaning. In addition, when using ammonium perrhenate the use of reductant such as hydrogen can be avoided. The method using ammonium perrhenate uses less catalyst and results in cleaner reactors post reaction, thus less downtime is needed to service the equipment.

In one embodiment of the present invention, the catalyst is used at a ratio of 1.0 to 50 mol-% per mucic acid or mucic acid ester.

In one embodiment of the present invention, the solvent is selected from methanol, ethanol or butanol.

In one embodiment of the present invention, the reductant is hydrogen, when methyltrioxorhenium is used as the catalyst.

One major advantage of using the above mentioned combination is that the hydrogen, when used, results in $H_2O$ as a by-product, thus leaving only an alcohol solvent, such as butanol, which is easy to wash or distil off in the purification steps. Hydrogen can also be recycled and it is cheaper compared to other prior art reductants, such as 1-butanol. Other reductants than alcohols are also problematic in the purification step and must be physically removed. Thereby the present method is particularly green and produces only low amounts of waste. A further advantage is achieved when using ammonium perrhenate as the reaction catalyst in that it does not require the use of hydrogen, and is heterogeneous thus being easily extracted from the reaction mixture.

The present separation and purification method is based on utilizing high vacuum distillation, which prevents the destruction of the muconic acid ester due to high temperature needed for normal distillation. In addition, solidification of the product into the distillation equipment is avoided by keeping all the equipment hot, in other words by using a total heating environment, which enables the solidification to happen only in the receiving vessel.

According to one embodiment of the present invention, the present method includes separation and purification of muconic acid from a crude reaction mixture, wherein the method includes isolating muconic acid ester by high vacuum distillation in a total heating environment.

According to one embodiment of the present invention, the high vacuum distillation is carried out at pressure lower than 4 mbar, preferably lower than 3 mbar, and most suitably lower than 1 mbar. High vacuum distillation minimizes thermal decomposition at elevated temperatures.

The total heating environment herein means that the distillation apparatus is not cold anywhere i.e. has no temperature gradients, but instead it is uniformly heated. By doing such, crystallization of the product into places which could become blocked inside the distillation equipment is avoided, and instead the solidification only happens in the receiving vessel.

One embodiment of the present invention is to use surround-heating distillation equipment. For example, Kugelrohr distillation is one good example of a distillation apparatus, which keeps the whole apparatus at the same temperature, which is ideal when distilling material with a high melting point at room temperature. By doing so, muconic acid ester can be isolated successfully and in an efficient manner.

Another advantage of the present invention is that no distillation aids are required.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in generating a full value chain from the forest industry, agriculture, or food industry side-streams to platform chemicals and end applications. In principle, this chain comprises converting the aldaric acids or the ester there of, such as mucic acid, into muconic acid, which in turn is used as platform chemicals for various bio-based applications, such as bio-based polyesters and nylon, as well as for pharmaceutical building blocks.

EXAMPLES

The GC-FID and GC-MS analyses were done with Shimadzu GC-1020 Plus Gas Chromatograph equipped with FID or MS analyser. The column used was ZB-5HT Inferno and the temperature program 100° C./1 min->10° C./min to 280° C./hold time 1 min->30° C./min to 350° C./hold time 5 min. When using FID analyser the following parameters were used Injector temperature 320° C., detector temperature 380° C., carrier gas helium, pressure 100.2 kPa, total flow 103.8 ml/min, column flow 1.00 ml/min, linear velocity 27.5 cm/sec, purge flow 3.0 ml/min, injection volume 1.0 μl, split ratio 100. When using MS-detector the following parameters where used injector temperature 260° C., detector temperature 250° C., carrier gas helium, pressure 60 kPa, total flow 10 ml/min, column flow 1.00 ml/min, linear velocity 39 cm/sec, purge flow 3.0 ml/min, injection volume 1.0 μl, split ratio 5.0. All reaction fractions were silylated with standard methods prior to GC-FID and GC-MS analysis. $^1$H NMR analysis has been undertaken where appropriate.

1. Synthesis of Mucic Acid Esters

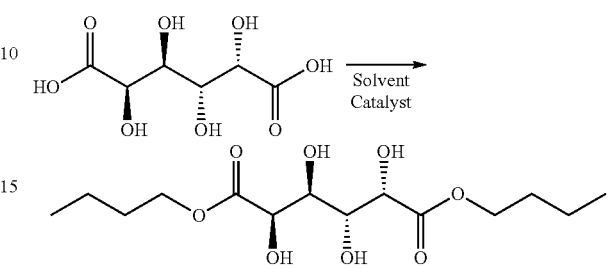

Mucic acid (95.2 mmol) and phenyl sulfonic acid ethyl sulphide silica was added to butanol (500 cm$^3$), and the resulting suspension stirred and heated up to 75-90° C. After 48 hours, the reaction was cooled down to about 40° C. and was filtered by hot vacuum filtration on glass porosity 1 sinter. The solvent of the filtrate was evaporated by using rotary evaporator to afford an off-white solid, 95% yield, GC-FID retention time 14.8 minutes, $^1$H NMR δ 1.0 (6H, m, CH$_3$), 1.4 (4H, m, —CH$_2$—), 1.7 (4H, m, —CH$_2$—), 10.0 (2H, s, —OH), 11.0 (2H, s, —OH).

2. MTO Catalysed Synthesis of Muconic Acid (Ester)

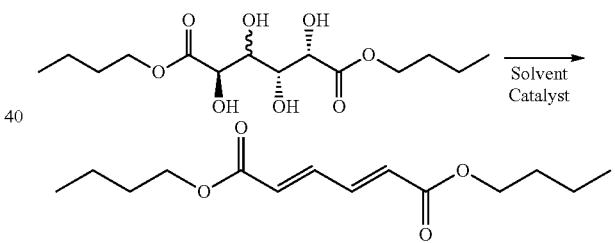

Mucic acid butyl ester or saccharic acid butyl ester (3.1 mmol) was added with MTO (100 wt %) to butanol (30 cm$^3$) and pressurized with about 5 bar hydrogen gas, the reaction mixture was stirred (400 rpm) and heated to 120° C. After 6 hours the reaction was stopped and the reactor cooled down. The reactor was then depressurized and the reaction mixture filtered under vacuum and evaporated by rotary evaporation (T=43° C.). The resulting dark semi-solid/solid was then purified.

Example syntheses are tabulated below in table 1.

TABLE 1

| Substrate | Catalyst/ loading mol-% | Solvent/ loading equivalents | Acid catalyst/ wt-% | Temperature/° C. | Time/ h | Yield of muconic acid ester |
|---|---|---|---|---|---|---|
| Mucic acid butyl ester | 25 | 30 | — | 120 | 6 | 57.3 |
| | 10 | 30 | — | 120 | 6 | 11.8 |
| | 50 | 15 | — | 120 | 6 | 83.1 |
| | 50 | 30 | H$_2$SO$_4$, 10 | 120 | 5 | 65.5 |

TABLE 1-continued

| Substrate | Catalyst/ loading mol-% | Solvent/ loading equivalents | Acid catalyst/ wt-% | Temperature/° C. | Time/ h | Yield of muconic acid ester |
|---|---|---|---|---|---|---|
| | 20 | 30 | — | 120 | 6 | 54.5 |
| | 50 | 7 | — | 120 | 6 | 85.0 |
| | 50 | 5 | — | 120 | 6 | 61.9 |
| | 25 | 30 | p-TSA, 10 | 120 | 6 | 57.4 |
| | 25 | 7 | — | 120 | 6 | 33.1 |
| Saccharic acid butyl ester | 50 | 30 | — | 120 | 6 | 12.4 |

3. Ammonium Perrhenate Catalyzed Synthesis of Muconic Acid (Ester)

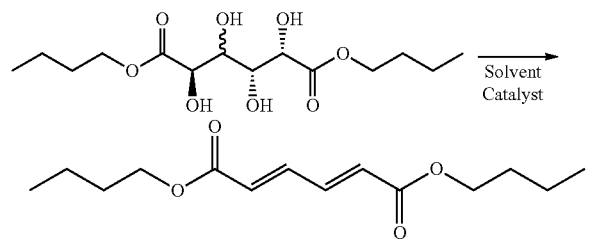

Mucic acid butyl ester or saccharic acid butyl ester (3.1 mmol) was added with ammonium perrhenate (100 wt-%) to butanol (30 cm$^3$) and pressurized with about 5 bar nitrogen gas, the reaction mixture was stirred (400 rpm) and heated to the specified temperature. After the desired amount of time the reaction was stopped and the reactor cooled down. The reactor was then depressurized, vacuum filtered and the reaction mixture evaporated by rotary evaporation (T=43° C.). The product was then purified.

Example syntheses are tabulated below in table 2.

TABLE 2

| Substrate | Catalyst/ loading mol-% | Solvent/ loading equivalents | Temperature/ ° C. | Time/ h | Yield of muconic acid ester |
|---|---|---|---|---|---|
| Mucic acid butyl ester | 100 | 30 | 150 | 6 | 13.6 |
| | 50 | 15 | 175 | 24 | 60.1 |
| | 50 | 7 | 175 | 24 | 16.0 |
| | 25 | 15 | 175 | 24 | 59.0 |
| | 15 | 15 | 175 | 24 | 50.0 |
| | 15 | 15 | 175 | 12 | 49.4 |
| | 50 | 15 | 200 | 2 | 55.8 |
| | 25 | 15 | 175 | 8 | 54.4 |
| | 15 | 15 | 220 | 2 | 7.6 |
| | 15 | 15 | 175 | 24 | 19.3 |
| Saccharic acid butyl ester | 100 | 15 | 200 | 24 | 4.3 |
| | 100 | 15 | 150 | 48 | 2.8 |
| | 100 | 15 | 175 | 48 | 3.8 |

4. Purification of Muconic Acid (Ester) Reaction Mass

The purification method outlined below can be applied to each of the above crude reaction products. Technically, any synthesis of crude muconic acid ester can be purified by the method outlined below. For illustration, the synthesis of muconic acid diester is outlined in detail in the separate patent WO 2015/189481.

The crude muconic acid ester oil (1.29 g) was placed in a distillation bulb and the apparatus set-up for bulb-to-bulb distillation in the oven. The bulbs were set to stir between 1-40 rpm and a vacuum was gently applied. Over 5 minutes the vacuum was lowered to 3.4 mbar or lower. Finally, the pressure was set to 1 mbar or below. The temperature was increased in a stepwise until a yellow solid starts to appear the in the adjacent bulb at 166-170° C. The bulb was then slid out of the oven and cooled to about 0° C. The temperature was maintained until all muconic dibutyl ester had been distilled across. The muconic acid ester was isolated as an off-white solid, 27% recovery, mass recovery of 60.5% based on GC-FID, 1H NMR: δ 0.9 (6H, m, CH3), 1.4 (4H, m, —CH2—), 1.7 (4H, m, —CH2—), 4.2 (4H, m, —CH2—), 6.2 (2H, d, alkene-H), 7.3 (2H, d, alkene-H), GCMS: mz 254.

CITATION LIST

Patent Literature

WO 2015/189481
WO 2017/207875

The invention claimed is:

1. A method for producing muconic acid ester from aldaric acid, the method comprising:
   esterification of aldaric acid into aldaric acid ester,
   catalytic dehydroxylation of the aldaric acid ester by heating the aldaric acid ester with a solvent and optionally an acidic catalyst in a pressurized container to a temperature between 100 to 250° C. in the presence of a transition metal catalyst for a pre-determined reaction time, and
   purifying the produced muconic acid ester in a total heating environment.

2. The method according to claim 1, wherein the catalyst comprises ammonium perrhenate or methyltrioxorhenium (MTO).

3. The method according to claim 2, wherein the temperature is between 90 and 150° C. ° C. when MTO is employed.

4. The method according to claim 2, wherein the temperature is between 150 and 250° C. ° C. when ammonium perrhenate is employed.

5. The method according to claim 1, wherein the catalyst is used at a ratio of 1.0 to 100 mol-% per aldaric acid ester.

6. The method according to claim 1, wherein the solvent is selected from a short chain alcohol under C4 in length.

7. The method according to claim 1, further comprising adding hydrogen as a reductant.

8. The method according to claim 1, wherein the pressure inside the container is adjusted to a level of 1 to 50 bars with hydrogen gas if MTO is the catalyst.

9. The method according to claim 1, wherein the reaction time is between 1 minute and 70 hours.

10. The method according to claim 1, the muconic acid ester is produced from mucic acid ester.

11. A method for separating and purifying muconic acid ester from a crude reaction mixture comprising isolating muconic acid ester by high vacuum distillation in a total heating environment.

12. The method according to claim 11, wherein the high vacuum distillation is carried out at pressure lower than 4 mbar.

13. The method according to claim 11, wherein the distillation is carried out at a temperature of 180° C. or lower.

14. The method according to claim 11, wherein the distillation is carried out without any distillation aids.

15. The method according to claim 11, wherein the distillation is carried out by using total heating and/or surround-heating distillation equipment.

16. The method according to claim 2, wherein the reaction time is from 2 to 12 hours when MTO is employed.

17. The method according to claim 2, wherein the reaction time is from 2 to 6 hours when ammonium perrhenate is employed.

18. The method according to claim 2, wherein the catalyst is used at a ratio of 25-50 mol-% when MTO is employed.

19. The method according to claim 1, wherein the purifying is done by vacuum distillation in a uniformly heated environment having no temperature gradients.

\* \* \* \* \*